(12) United States Patent
Levin et al.

(10) Patent No.: US 6,441,251 B1
(45) Date of Patent: Aug. 27, 2002

(54) PRODUCTION OF PHENOL

(75) Inventors: Doron Levin, Annandale, NJ (US); Jose G. Santiesteban, Bethlehem, PA (US); Lei Zhang, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/946,711

(22) Filed: Sep. 4, 2001

(51) Int. Cl.⁷ .............................................. C07C 37/08
(52) U.S. Cl. ...................... 568/798; 568/385; 568/485; 568/741; 568/754
(58) Field of Search ................. 568/798, 385, 568/485, 741, 754

(56) References Cited

U.S. PATENT DOCUMENTS

| | | | |
|---|---|---|---|
| 4,490,565 A | 12/1984 | Chang et al. | 568/798 |
| 4,490,566 A | 12/1984 | Chang et al. | 568/798 |
| 4,898,995 A | 2/1990 | Knifton et al. | 568/798 |
| 5,057,296 A | 10/1991 | Beck | 423/277 |
| 5,098,684 A | 3/1992 | Kresge et al. | 423/277 |
| 5,102,643 A | 4/1992 | Kresge et al. | 423/328 |
| 5,198,203 A | 3/1993 | Kresge et al. | 423/718 |
| 5,304,363 A | 4/1994 | Beck et al. | 423/328.1 |
| 6,169,215 B1 | 1/2001 | Levin et al. | 568/798 |
| 6,169,216 B1 | 1/2001 | Levin et al. | 568/798 |

OTHER PUBLICATIONS

Neftekhimiya, "Decomposition of Cumyl Hydroperoxide in the presence of Sulfonated Silica in Flow–Type Systems," 1993, No. 1, 33:41–45.

*Primary Examiner*—Sreeni Padmanabhan
(74) *Attorney, Agent, or Firm*—Darryl M. Tyus

(57) ABSTRACT

A process for producing phenol and acetone from cumene hydroperoxide is described in which the cumene hydroperoxide is contacted with a solid-acid catalyst comprising an inorganic, porous, crystalline material, designated as M41S, exhibiting, after calcination, an x-ray diffraction pattern with at least one peak at a d-spacing greater than about 18 Angstrom Units with a relative intensity of 100 and a benzene adsorption capacity of greater than 15 grams of benzene per 100 grams of said material at 50 torr and 25° C., wherein said material comprises sulfonate functionality.

7 Claims, No Drawings

PRODUCTION OF PHENOL

FIELD OF THE INVENTION

This invention relates to the production of phenol and more particularly to a process for producing phenol and acetone from cumene hydroperoxide.

BACKGROUND OF THE INVENTION

Phenol is an important organic chemical with a wide variety of industrial uses. It is used, for example, in the production of phenolic resins, bisphenol-A and caprolactam. A number of processes are currently in use for the production of phenol but the process providing the largest proportion of the total production capacity is the cumene process which now accounts for over three quarters of the total U.S. production. The basic reaction involved in this process is the cleavage of cumene hydroperoxide into phenol and acetone:

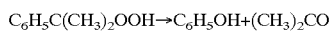

$$C_6H_5C(CH_3)_2OOH \rightarrow C_6H_5OH + (CH_3)_2CO$$

On the industrial scale, the cumene hydroperoxide is usually treated with dilute sulphuric acid (5 to 25 percent concentration) at a temperature of about 50° C. to 70° C. After the cleavage is complete, the reaction mixture is separated and the oil layer distilled to obtain phenol and acetone together with cumene, alpha-methylstyrene, acetophenone and tars. The cumene may be recycled for conversion to the hydroperoxide and subsequent cleavage. The phenol produced in this way is suitable for use in resins although further purification is required for pharmaceutical grade product.

Although the process described above is capable of producing both phenol and acetone in good yields, it would be desirable to find a process that would reduce the need for the product separation and purification steps inherent in a homogeneous process and that would avoid the need for environmentally hazardous liquid acid catalysts.

The heterogeneous cleavage of cumene hydroperoxide (CHP) over various solid acid catalysts has already been reported. For example, U.S. Pat. No. 4,490,565 discloses the use of zeolite beta in the cleavage of cumene hydroperoxide, whereas U.S. Pat. No. 4,490,566 discloses the use of a Constraint Index 1–12 zeolite, such as ZSM-5, in the same process.

In addition, U.S. Pat. Nos. 6,169,215 and 6,169,216 disclose cumene hydroperoxide cleavage over solid acid catalysts formed by modifying a Group IVB metal oxide with a Group VIB metal oxyanion and by sulfating transition metal oxides.

Solid acid catalysts having sulfonic acid groups have also been proposed for use in cumene hydroperoxide cleavage. For example, U.S. Pat. No. 4,898,995 discloses a process for the coproduction of phenol and acetone by reacting cumene hydroperoxide over a heterogeneous catalyst comprising an ion exchange resin with sulfonic acid functionality. In such a catalyst the sulfonic acid functional group is bonded to an organic, preferable polystyrene or styrene-divinylbenzene, polymer backbone. Given the organic nature of this support, these catalysts are sensitive to temperature, and typically cannot be used above In addition, the article entitled "Decomposition of Cumyl Hydroperoxide in the presence of Sulfonated Silica in a Flow-Type System", from Neftekhimiya, 33, No. 1, 41–45, 1993 discloses cumene hydroperoxide cleavage over a catalyst obtained by modifying amorphous silica with a chlorosilane and then treating the modified silica with chlorosulfonic acid. However, as discussed in more detail below, tests with amorphous silica catalysts having sulfonic acid functionality have shown the catalysts to have only limited activity for the cleavage reaction.

Accordingly, there is an ongoing need for a solid-acid cumene hydroperoxide cleavage catalyst that exhibits the required combination of activity and selectivity to provide an acceptable replacement for sulfuric acid catalysts.

SUMMARY OF THE INVENTION

The present invention is directed to a process for producing phenol and acetone from cumene hydroperoxide, wherein the process comprises the step of contacting cumene hydroperoxide with a solid-acid catalyst comprising an inorganic, porous, crystalline material, designated as M41S, exhibiting, after calcination, an x-ray diffraction pattern with at least one peak at a d-spacing greater than about 18 Angstrom Units with a relative intensity of 100 and a benzene adsorption capacity of greater than 15 grams of benzene per 100 grams of said material at 50 torr and 25° C., wherein said material comprises sulfonate functionality.

The process of the invention achieves enhanced conversion of cumene hydroperoxide to phenol and acetone. Although the reason for this improvement is not fully understood, it is believed that the exceptionally high surface area of the M41S type materials allows for correspondingly high numbers of sulfonic acid groups and hence for an enhanced acid activity.

Preferably, the porous, crystalline material has uniform pores within the range of from about 13 Angstroms to about 200 Angstroms, more usually from about 15 Angstroms to about 100 Angstroms.

Preferably, the porous, crystalline material has, after calcination, a hexagonal arrangement of uniformly-sized pores having diameter of at least about 15 Angstrom Units and exhibits a hexagonal electron diffraction pattern that can be indexed with a $d_{100}$ value greater than about 18 Angstrom Units.

Preferably, the porous crystalline material is a silicate or aluminosilicate.

Preferably, said contacting step is conducted at a temperature of 20° C. to 150° C. and a pressure of atmospheric to 1000 psig (100 to 7000 kPa) and more preferably at a temperature of 40° C. to 120° C. and a pressure of atmospheric to 400 psig (100 to 2860 kPa).

DESCRIPTION OF THE INVENTION

The present invention provides an improved process for producing phenol and acetone from cumene hydroperoxide, wherein the process comprises the step of contacting cumene hydroperoxide with a solid-acid catalyst comprising an inorganic, porous, crystalline material, designated as M41S, exhibiting, after calcination, an x-ray diffraction pattern with at least one peak at a d-spacing greater than about 18 Angstrom Units with a relative intensity of 100 and a benzene adsorption capacity of greater than 15 grams of benzene per 100 grams of said material at 50 torr and 25° C., wherein said material comprises sulfonate functionality.

M41S materials and their synthesis are described in U.S. Pat. No. 5,102,643, the entire contents of which are incorporated herein by reference. M41S materials are mesoporous and for use herein preferably have uniform pores within the range of from about 13 Angstroms to about 200 Angstroms, more usually from about 15 Angstroms to about 100 Angstroms. Control of the pore size within the above range is conveniently achieved by the process described in U.S. Pat. No. 5,057,296, the entire contents of which are also incorporated herein by reference.

In their calcined form, M41S materials have the following composition:

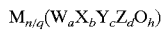

wherein W is a divalent element, such as a divalent first row transition metal, e.g. manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and (a+b+c+d)=1. In a preferred embodiment, the porous crystalline material used herein has a composition wherein a and d=0, and h=2, namely the material is a silicate or metallosilicate, preferably an aluminosilicate.

A preferred form of the crystalline material for use in the process of the invention exhibits, after calcination, a hexagonal arrangement of uniformly-sized pores having diameter of at least about 15 Angstrom Units and exhibits a hexagonal electron diffraction pattern that can be indexed with a $d_{100}$ value greater than about 18 Angstrom Unit. This material, identified as MCM-41, and its preparation and properties are described in further detail in U.S. Pat. No. 5,098,684, incorporated herein by reference.

Alternatively, the crystalline material used in the process of the invention can have the cubic arrangement of pores as described in U.S. Pat. No. 5,198,203 or the lamellar structure as described in U.S. Pat. No. 5,304,363, both of which patents are incorporated herein by reference.

In the solid acid catalyst used in the process of the invention, the porous crystalline material is functionalized by the introduction of sulfonyl groups. This can be achieved by any method known in the art for introducing sulfonate functionality. Such methods include (1) reacting mercaptans, sulfides, disulfides, sulfoxides or sulfones with oxidizing agents such as potassium permanganate, chromic anhydride, aqueous bromine, hydrogen peroxide and nitric acid, (2) reacting alkylhalides with sodium, potassium or ammonium sulfite in aqueous ethanol solution under refluxing conditions (the Strecker reactions), and (3) the addition of bisulfites to unsaturated compounds such as olefins in the presence of oxygen or other oxidizing agents to give the corresponding alkylsulfonic acid. For example, where the porous crystalline material is a silicate or metallosilicate, the material can be reacted with a mercaptoalkoxysilane, such as (3-mercaptopropyl)trimethoxysilane, and the resultant thiol groups bonded to the surface of the material can be oxidized to the desired sulfonyl groups with hydrogen peroxide.

The cleavage reaction of the invention is typically effected by contacting the cumene hydroperoxide with the solid acid catalyst described above in the liquid phase at a temperature of 20° C. to 150° C. and a pressure of atmospheric to 1000 psig (100 to 7000 kPa) and more preferably at a temperature of 40° C. to 120° C. and a pressure of atmospheric to 400 psig (100 to 2860 kPa). To effect the contacting of the cumene hydroperoxide, the solid acid catalyst described above may be contained in a stationary or fluidized bed, and the contacting operation may take place continuously or batch-wise. If the contacting takes place continuously, the liquid hourly space velocity (LHSV) based on cumene hydroperoxide is within the range of 0.1 to 100 hr$^{-1}$, preferably 1 to 50 hr$^{-1}$. If the contacting takes place batch-wise, the residence time is within the range of 1 to 360 min, preferably 1 to 180 min. The cumene hydroperoxide is preferably dissolved in an organic solvent inert to the cleavage reaction, such as benzene, toluene, acetone and most preferably acetone. The use of a solvent is preferred to assist in dissipating the heat of reaction (about 60 kcal/mol).

The invention will now be more particularly described with reference to the following Examples.

EXAMPLE 1

MCM-41 material having a nominal pore size of 80 Å was synthesized from an inorganic siliceous precursor using an organic cationic trimethylammonium surfactant ($C_{16}H_{33}N(CH_3)_3Cl$) as a supramolecular templating agent and an auxiliary organic swelling agent (mesitylene). Eighty grams of a 29% cetyltrimethylammonium hydroxide solution were charged in a 500 ml beaker. Then, 1.65 g USALCO (sodium aluminate), 40.0 g of tetramethylammonium silicate (10% silica), 10 g of Hisil (~90% silica), 150 g of water and finally 50 gram of mesitylene were added stepwise to the above solution at room temperature with stirring. After stirring for 10 minutes, the reaction mixture was transferred to a 600 ml autoclave and hydrothermally treated at 105° C. for 72 hrs with stirring at 150 RPM. The solid powder obtained was filtered, washed with water and acetone, and then calcined at 540° C. in air for 6 hours to remove the organic template. The silica to alumina molar ratio of the MCM-41 was determined to be 100. The large pore size of the MCM-41 was confirmed by X-ray diffractometry (XRD). The sample had a Brunauer-Emmett-Teller (BET) surface area of 750 m$^2$/g.

EXAMPLE 2

Five grams of the material of Example 1 were hydrated by refluxing in 250 ml of distilled water for 4 hours. The hydrated MCM-41 powder was recovered by filtration and dispersed in 250 ml of toluene in a Dean-Stark distillation apparatus. Excess water adsorbed on the MCM-41 material was removed until the MCM-41 powder was homogeneously dispersed in the translucent solution. After the solution cooled to room temperature (about 25° C.), 28.6 gm of (3-mercaptopropyl)trimethoxy-silane (MPTS) was added. The mixture was stirred overnight at ambient conditions, followed by refluxing for 4 hrs. The unreacted MPTS was removed by Soxhlet extraction with 2-propanol for 24 hrs. The thiol groups anchored on the surface of the MCM-41 material were further oxidized to SO$_3$ groups by the addition of a 30% H$_2$O$_2$ aqueous solution with methanol as a co-solvent (1:3 g/g). After being thoroughly washed with deionized (DI) water and ethanol, the recovered material (1 wt %) was added into a 0.1 M H$_2$SO$_4$ aqueous solution, and stirred for 4 hrs. The final acidified sulfonated MCM-41 was washed with DI water until the pH of the effluent solution was neutral. The catalyst was dried at 80° C. overnight.

EXAMPLE 3

MCM-41 material having a nominal pore size of 40 Å was synthesized from an inorganic siliceous precursor using an organic cationic trimethylammonium surfactant ($C_{16}H_{33}N(CH_3)_3Cl$) as a supramolecular templating agent. 5900 g of distilled water and 1860 g of 25% tetramethylammonium hydroxide were charged in a 5 gal. autoclave. 240 g USALCO (sodium aluminate) and 200 g of Ultrasil were slowly added to the above solution at room temperature with vigorous stirring. After stirring for 55 minutes, 5000 g of Arqad 16/29 (29% $C_{16}H_{33}N(CH_3)_3Cl$ aqueous solution) was gradually introduced to the solution. The sample was hydrothermally treated at 143° C. for 14 hrs with stirring at 50 RPM. The solid powder obtained was diluted with 20 gal of water, filtered, and then calcined at 540° C. in air for 6 hours to remove the organics. The silica to alumina molar ratio of the MCM-41 was determined to be 24. The long-range pore packing order of the MCM41 was characterized by X-ray diffractometry (XRD). The sample had a Brunauer-Emmett-Teller (BET) surface area of 803 $m^2/g$.

EXAMPLE 4

Seven grams of the material of Example 3 was hydrated by refluxing in 250 ml of distilled water for 4 hrs. The hydrated MCM-41 powder was recovered by filtration and dispersed in 300 ml of toluene in a Dean-Stark distillation apparatus. Excess water adsorbed on the MCM-41 material was removed until the MCM-41 powder was homogeneously dispersed in the translucent solution. After the solution cooled to room temperature, 40 gm of (3-mercaptopropyl)trimethoxysilane (MPTS) was added. The mixture was stirred overnight at ambient conditions, followed by refluxing for 4 hrs. The unreacted MPTS was removed by Soxhlet extraction with 2-propanol for 24 hrs. The thiol groups anchored on the surface of the MCM-41 material were further oxidized to $SO_3$ groups by the addition of a 30% $H_2O_2$ aqueous solution with methanol as a co-solvent (1:3 gm/gm). After being thoroughly washed with DI water and ethanol, the recovered material (1 wt %) was added into a 0.1 M $H_2SO_4$ aqueous solution, and stirred for 4 hrs. The final acidified sulfonated MCM-41 was washed with DI water until the pH of the effluent solution was neutral. The catalyst was dried at 80° C. overnight.

EXAMPLE 5

Comparative

A porous organic-inorganic hybrid silica containing SH and $SO_3$ groups was synthesized via a sol-gel route. Tetraethoxysilane (TEOS), (3-mercaptopropyl)-trimethoxysilane (MPTS), and 2-(4-chlorosulfonylphenyl) ethyltrimethoxysilane (CSPTS) were used as the sol-gel precursors. 20.83 gm of TEOS was dissolved in 18.4 gm of ethanol to which 4.91 gm of MPTS was added with vigorous stirring for 10 minutes. The precursor mixture was hydrolyzed by the addition of 19.8 gm of DI water and 0.05 gm of 37% HCl aqueous solution. After 20 minutes of stirring, 16.24 gm of 50% CSPTS in $CH_2Cl_2$ was introduced dropwise. The molar ratio of the wet gel can be represented as 1 TEOS: 0.25 MPTS: 0.25 CSPTS: 4 EtOH: 11 $H_2O$: 0.005 HCl. The reactant mixture gelled within 48 hrs and was further aged at ambient conditions for 48 hrs. The gel monolith was then ground to a powder and dried at 80° C. overnight. The final product obtained was washed with ethanol and DI water until the pH of the effluent was neutral. The catalyst was dried at ambient conditions overnight.

EXAMPLE 6

To a 250-ml, round-bottom flask fitted with a condenser, stirrer and dropping funnel, and located in a water bath for temperature control, was charged a mixture of 100.0 gm of acetone and 1.00 gm of the catalyst of Example 2. The mixture was heated to reflux (57° C.) with stirring, and 50.0 gm of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 gm/min. Following addition of the CHP solution, small samples (~0.2 ml) of the reactant solution were withdrawn at regular intervals, filtered, and analyzed by GC.

Table 1 below shows the composition (mass %) of the reactant solution at 10 and 60 minutes after the addition of the CHP was complete.

TABLE 1

|  | Feed | 10 min | 60 min |
| --- | --- | --- | --- |
| Acetone | 66.67 | 77.55 | 77.72 |
| Cumene | 2.56 | 2.60 | 2.58 |
| Phenol | 0.09 | 15.85 | 16.56 |
| A-Methyl Styrene | 0.07 | 0.48 | 0.87 |
| Acetophenone | 0.69 | 1.39 | 1.11 |
| 2-Phenyl-2-Propanol | 2.36 | 0.89 | 0.59 |
| Cumene Hydroperoxide | 26.93 | 0.62 | 0.04 |
| CHP Conversion |  | 97.7% | 99.9% |

EXAMPLE 7

To a 250-ml, round-bottom flask fitted with a condenser, stirrer and dropping funnel, and located in a water bath for temperature control, was charged a mixture of 100.0 gm of acetone and 1.00 gm of the catalyst of Example 4. The mixture was heated to reflux (57° C.) with stirring, and 50.0 gm of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 gm/min. Following addition of the CHP solution, small samples (~0.2 ml) of the reactant solution were withdrawn at regular intervals, filtered, and analyzed by GC.

Table 2 below shows the composition (mass %) of the reactant solution at 10 and 60 minutes after the addition of the CHP was complete.

TABLE 2

|  | Feed | 10 min | 60 min |
| --- | --- | --- | --- |
| Acetone | 66.67 | 71.71 | 77.12 |
| Cumene | 2.56 | 2.65 | 2.62 |
| Phenol | 0.09 | 6.82 | 16.73 |
| A-Methyl Styrene | 0.07 | 0.36 | 0.70 |
| Acetophenone | 0.69 | 3.60 | 1.33 |
| 2-Phenyl-2-Propanol | 2.36 | 2.40 | 0.76 |
| Cumene Hydroperoxide | 26.93 | 10.34 | 0.07 |
| CHP Conversion |  | 61.6% | 99.8% |

EXAMPLE 8

Comparative

To a 250-ml, round-bottom flask fitted with a condenser, stirrer and dropping funnel, and located in a water bath for temperature control, was charged a mixture of 100.0 gm of acetone and 1.00 gm of the catalyst of Example 5. The mixture was heated to reflux (57° C.) with stirring, and 50.0 gm of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table 3 below shows the composition (mass %) of the reactant solution at 10 and 60 minutes after the addition of the CHP was complete.

TABLE 3

|  | Feed | 10 min | 60 min |
|---|---|---|---|
| Acetone | 66.67 | 68.75 | 72.28 |
| Cumene | 2.56 | 2.59 | 2.66 |
| Phenol | 0.09 | 3.54 | 9.16 |
| A-Methyl Styrene | 0.07 | 0.39 | 0.44 |
| Acetophenone | 0.69 | 2.98 | 3.00 |
| 2-Phenyl-2-Propanol | 2.36 | 2.29 | 1.90 |
| Cumene Hydroperoxide | 26.93 | 17.80 | 8.79 |
| CHP Conversion |  | 33.9% | 67.4% |

It will be seen from Table 3 that the sulfonated silica catalyst of Example 5 was less active and selective in the conversion of CHP to phenol and acetone than the sulfonated MCM-41 catalysts of Examples 2 and 4.

EXAMPLE 9

The catalyst used in Example 6 was recovered by filtration, washed with acetone, and dried at 110° C. for 30 minutes. The recovered catalyst (0.93 gm) and 100.0 gm of acetone were charged to a 250-ml, round-bottom flask fitted with a condenser, stirrer and dropping funnel, and located in a water bath for temperature control. The mixture was heated to reflux (57° C.) with stirring, and 50.0 gm of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 gm/min. Following addition of the CHP solution, small samples (~0.2 ml) of the reactant solution were withdrawn at regular intervals, filtered, and analyzed by GC.

Table 4 below shows the composition (mass %) of the reactant solution at 10 and 60 minutes after the addition of the CHP was complete.

TABLE 4

|  | Feed | 10 min | 60 min |
|---|---|---|---|
| Acetone | 66.67 | 73.65 | 77.75 |
| Cumene | 2.56 | 2.62 | 2.58 |
| Phenol | 0.09 | 10.42 | 16.35 |
| A-Methyl Styrene | 0.07 | 0.33 | 0.55 |
| Acetophenone | 0.69 | 2.79 | 1.13 |
| 2-Phenyl-2-Propanol | 2.36 | 1.95 | 0.90 |
| Cumene Hydroperoxide | 26.93 | 6.68 | 0.04 |
| CHP Conversion |  | 75.2% | 99.8% |

The recovered catalyst showed lower initial activity than the fresh catalyst, but reached the same conversion level after 60 minutes.

EXAMPLE 10

Comparative

The MCM-41 starting materials (without sulfonic acid functionality) used to prepare the catalysts in Examples 2 and 4 were tested for catalytic activity. To a 250-ml, round-bottom flask fitted with a condenser, stirrer and dropping funnel, and located in a water bath for temperature control, was charged a mixture of 100.0 gm of acetone and 1.0 gm of the parent MCM-41 material of Example 1 or 3. The mixture was heated to reflux (57° C.) with stirring, and 50.0 gm of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 gm/min. Following addition of the CHP solution, small samples (~0.2 ml) of the reactant solution were withdrawn at regular intervals, filtered, and analyzed by GC.

Table 5 below shows the composition (mass %) of the reactant solution at 60 minutes after the addition of the CHP was complete.

TABLE 5

|  | Feed | Example 1 Material | Example 3 Material |
|---|---|---|---|
| Acetone | 66.67 | 65.89 | 66.85 |
| Cumene | 2.56 | 2.53 | 2.59 |
| Phenol | 0.09 | 0.35 | 1.88 |
| A-Methyl Styrene | 0.07 | 0.12 | 0.16 |
| Acetophenone | 0.69 | 0.88 | 1.36 |
| 2-Phenyl-2-Propanol | 2.36 | 2.36 | 2.38 |
| Cumene Hydroperoxide | 26.93 | 27.56 | 24.19 |
| CHP Conversion |  | Negligible | 10.2% |

This comparative example shows that without sulfonic acid functionality, the parent MCM-41 materials have very little to no activity for CHP decomposition.

What we claim is:

1. A process for producing phenol and acetone from cumene hydroperoxide, wherein said process comprises the step of contacting cumene hydroperoxide with a solid-acid catalyst comprising an inorganic, porous, crystalline material exhibiting, after calcination, an x-ray diffraction pattern with at least one peak at a d-spacing greater than about 18 Angstrom Units with a relative intensity of 100 and a benzene adsorption capacity of greater than 15 grams of benzene per 100 grams of said material at 50 torr and 25° C., wherein said material comprises sulfonate functionality.

2. The process of claim 1, wherein the porous, crystalline material has uniform pores within the range of from about 13 Angstroms to about 200 Angstroms.

3. The process of claim 1, wherein the porous, crystalline material has uniform pores within the range of from about 15 Angstroms to about 100 Angstroms.

4. The process of claim 1, wherein the porous, crystalline material has, after calcination, a hexagonal arrangement of uniformly-sized pores having diameter of at least about 15 Angstrom Units and exhibits a hexagonal electron diffraction pattern that can be indexed with a $d_{100}$ value greater than about 18 Angstrom Units.

5. The process of claim 1, wherein the porous crystalline material is a silicate or aluminosilicate.

6. The process of claim 1, wherein said contacting step is conducted at a temperature of 20 to 150° C. and a pressure of atmospheric to 1000 psig.

7. The process of claim 1, wherein said contacting step is conducted at a temperature of 40 to 120° C. and a pressure of atmospheric to 400 psig.

* * * * *